(12) United States Patent
Schaefer et al.

(10) Patent No.: US 11,278,761 B2
(45) Date of Patent: Mar. 22, 2022

(54) APPARATUS AND METHOD FOR INCREASED REALISM OF TRAINING ON EXERCISE MACHINES

(71) Applicant: Crew Innovations LLC, Hailey, ID (US)

(72) Inventors: Michael V. Schaefer, Bremerton, WA (US); John A. Balint, Ketchum, ID (US)

(73) Assignee: CREW INNOVATIONS LLC, Hailey, ID (US)

( * ) Notice: Subject to any disclaimer, the term of this patent is extended or adjusted under 35 U.S.C. 154(b) by 159 days.

(21) Appl. No.: 16/841,653

(22) Filed: Apr. 6, 2020

(65) Prior Publication Data
US 2020/0230459 A1   Jul. 23, 2020

Related U.S. Application Data

(62) Division of application No. 15/567,826, filed as application No. PCT/US2016/028282 on Apr. 19, 2016, now Pat. No. 10,610,725.

(Continued)

(51) Int. Cl.
*A63B 22/00*   (2006.01)
*A63B 24/00*   (2006.01)
(Continued)

(52) U.S. Cl.
CPC ...... *A63B 22/0076* (2013.01); *A63B 22/0087* (2013.01); *A63B 24/0075* (2013.01);
(Continued)

(58) Field of Classification Search
CPC ............ A63B 21/0051; A63B 21/0053; A63B 21/0054; A63B 21/0055; A63B 21/0058; A63B 21/0087; A63B 21/0088; A63B 21/015; A63B 21/225; A63B 22/0076; A63B 22/0087; A63B 22/0605; A63B 24/0075; A63B 24/0084; A63B 24/0087; A63B 69/06; A63B 71/0622; A63B 2022/0079; A63B 2024/0009; A63B 2024/0012; A63B 2024/0081; A63B 2024/0093; A63B 2069/062; A63B 2069/064; A63B 2069/066;
(Continued)

(56) References Cited

U.S. PATENT DOCUMENTS 4,889,509 A * 12/1989 Pohlus ...................... B63B 1/14
                                                        440/105
4,984,986 A *  1/1991 Vohnout ................. A63B 24/00
                                                        434/247

(Continued)

*Primary Examiner* — Joshua Lee
(74) *Attorney, Agent, or Firm* — Cooper Legal Group, LLC

(57) ABSTRACT

An exercise machine includes a cyclical actuator and a mechanical energy storage device. Connective structure operatively connects the cyclical actuator to the mechanical energy storage device. Motion of the cyclical actuator urges physical motion of and energy storage in the mechanical energy storage device. The exercise machine further includes an electric machine. A communication pathway enables exchange of data between multiple associated exercise machines such that multiple associated operators on multiple associated exercise machines have a common experience.

17 Claims, 8 Drawing Sheets

Related U.S. Application Data

(60) Provisional application No. 62/149,869, filed on Apr. 20, 2015.

(51) Int. Cl.
  *G16H 20/30* (2018.01)
  *A63B 21/005* (2006.01)
  *A63B 71/06* (2006.01)
  *A63B 21/22* (2006.01)
  *A63B 22/06* (2006.01)
  *A63B 21/008* (2006.01)
  *A63B 21/015* (2006.01)
  *A63B 69/06* (2006.01)

(52) U.S. Cl.
  CPC ...... *A63B 24/0084* (2013.01); *A63B 24/0087* (2013.01); *G16H 20/30* (2018.01); *A63B 21/0051* (2013.01); *A63B 21/0053* (2013.01); *A63B 21/0054* (2015.10); *A63B 21/0055* (2015.10); *A63B 21/0058* (2013.01); *A63B 21/0087* (2013.01); *A63B 21/0088* (2013.01); *A63B 21/015* (2013.01); *A63B 21/225* (2013.01); *A63B 22/0605* (2013.01); *A63B 69/06* (2013.01); *A63B 71/0622* (2013.01); *A63B 2022/0079* (2013.01); *A63B 2024/0009* (2013.01); *A63B 2024/0012* (2013.01); *A63B 2024/0081* (2013.01); *A63B 2024/0093* (2013.01); *A63B 2069/062* (2013.01); *A63B 2069/064* (2013.01); *A63B 2069/066* (2013.01); *A63B 2069/068* (2013.01); *A63B 2071/063* (2013.01); *A63B 2071/0625* (2013.01); *A63B 2071/0638* (2013.01); *A63B 2071/0647* (2013.01); *A63B 2220/17* (2013.01); *A63B 2220/51* (2013.01); *A63B 2225/20* (2013.01); *A63B 2225/50* (2013.01); *A63B 2230/06* (2013.01)

(58) Field of Classification Search
  CPC ...... A63B 2069/068; A63B 2071/0625; A63B 2071/063; A63B 2071/0638; A63B 2071/0647; A63B 2220/17; A63B 2220/51; A63B 2225/20; A63B 2225/50; A63B 2230/06; G16H 20/30
  See application file for complete search history.

(56) References Cited

U.S. PATENT DOCUMENTS

| | | | | |
|---|---|---|---|---|
| 5,092,581 | A * | 3/1992 | Koz | A63B 69/06 434/247 |
| 5,382,211 | A * | 1/1995 | Solymosi | A63B 69/08 482/72 |
| 7,731,637 | B2 * | 6/2010 | D'Eredita | A63B 21/154 482/72 |
| 8,109,859 | B2 * | 2/2012 | Medina | A63B 22/0076 482/8 |
| 8,235,874 | B2 * | 8/2012 | D'Eredita | A63B 21/154 482/72 |
| 8,622,876 | B2 * | 1/2014 | Kelliher | A63B 23/12 482/72 |
| 2005/0016437 | A1 * | 1/2005 | Bishop | B63B 1/041 114/346 |
| 2007/0149364 | A1 * | 6/2007 | Blau | A63B 21/0053 482/57 |
| 2008/0280736 | A1 * | 11/2008 | D'Eredita | A63B 21/154 482/72 |
| 2011/0028278 | A1 * | 2/2011 | Roach | A63B 22/0076 482/72 |
| 2011/0118086 | A1 * | 5/2011 | Radow | A63B 21/0051 482/5 |
| 2013/0130206 | A1 * | 5/2013 | Smith | A63B 69/06 434/29 |

* cited by examiner

PRIOR ART

APPARATUS AND METHOD FOR INCREASED REALISM OF TRAINING ON EXERCISE MACHINES

CROSS-REFERENCE TO RELATED APPLICATIONS

This application claims the benefit of U.S. Provisional Application No. 62/149,869, filed Apr. 20, 2015, PCT Application No. PCT/US2016/028282, filed Apr. 19, 2016, and is a divisional application of U.S. Non-provisional application Ser. No. 15/567,826, filed Oct. 19, 2017, titled "Apparatus and Method for Increased Realism of Training on Exercise Machines," the entire disclosures of which are hereby incorporated herein by reference.

TECHNICAL FIELD

In various embodiments, the present disclosure relates generally to exercise machines, and more specifically to exercise machines that dissipate energy through mechanisms that allow customizable load profiles, and to exercise machines having an interconnection capability that enables synchronization of exercise activities.

BACKGROUND ART

Many athletic activities entail the coordination of motions by members of team. Herein, we term such activities "coordinated sport." To be competitive in coordinated sport, team members must build skill, strength, and endurance and learn to coordinate their efforts. An example of coordinated effort is, in team rowing, the performance of oarstrokes of closely similar timing, duration, and power. Another example is, in tandem bicycle riding, the coordination of pedal strokes. Herein, frequent reference will be made to the sport of rowing and to exercise machines pertinent to rowing, but such references are illustrative, not restrictive: other sports, non-sport activities, and types of exercise machines are contemplated and within the scope of the disclosure.

Teams may be trained by field exercise, e.g., actually rowing a boat on water; however, due to seasonal, weather, and other limitations on field exercise, in practice athletes prepare for and supplement field exercise by working out extensively on trainers, i.e., stationary machines whose mechanics simulate one or more aspects of the sport in question. A typical trainer comprises one or more mechanisms upon which the user's body rests and/or acts (e.g., pedals, oars, seats) and one or more dissipative mechanisms (e.g., air fins, friction pads), typically adjustable, which place energetic loads on the user. A typical trainer also comprises an inertial mechanism (e.g., flywheel) that simulates the inertia of one or more athletes in motion along with the inertia of a watercraft, bicycle, or other gear.

Trainers are most often built to accommodate a single athlete. Single-user trainers do not support training of team members in the coordinative aspects of a given sport, and when only single-user trainers are available, training in the coordinative aspects of the sport can only occur in field exercises. To overcome this problem, the prior art has developed team trainers, relatively large machines that accommodate two or more athletes at one time. For example, the rowing simulator disclosed in U.S. Pat. No. 8,622,876 describes mechanical ganging of single-oar rowing machines for simultaneous training of up to 8 rowers. However, in this example, dissipative loads (e.g., ergometers) are driven by each athlete: thus, the performance of one athlete does not dynamically affect the loads addressed by other athletes on the multi-user trainer. In another example, the simulated rowing machine disclosed in U.S. Pat. No. 8,235,874 describes ganging of single-oar rowing machines so as to include mechanical coupling of each rower's resistance and recovery mechanism to every other's, enabling the crew to align its power application in a realistic fashion.

Limitations of the prior art for coordinative (i.e., team) training include but are not limited to the following: (1) Athletes working out on isolated machines (e.g., in a single space but not mechanically connected, or in different geographical locations) cannot receive training on the coordination aspects of their sport. (2) All athletes to be trained by a team trainer must assemble at a common place and time to use the team trainer. This entails travel to the common location by all athletes and burdensome coordination of schedules. If one or more team members are not able to attend at the common place and time, training for full-team coordination cannot occur. (3) A training space must accommodate the bulk of the team trainer, whose maximum dimension, for an N-person trainer, will be on the order of N times that of a single-person trainer. (4) Realistic team trainers are significantly more costly on a per-athlete basis than individual trainers.

Techniques are therefore desired by means of which exercise machines can enable one or more athletes to receive realistic training on the coordinative aspects of their sport without requiring multiple athletes to assemble at a single location. Moreover, there is need for such exercise systems to be affordable and compact.

BRIEF SUMMARY

Technical Problem

Exercise machines constructed according to the prior art are generally provided with energy dissipation (i.e., load) devices that employ friction, gaseous, and/or liquid damping effects and whose rate of energy dissipation is approximately fixed after an initial adjustment, e.g., throughout a given exercise session. Also, such exercise machines generally include limited damping variability. Also, such exercise machines (herein also termed "trainers") are either inherently single-user (i.e., lack means of communication with other exercise machines that can be used to provide a common or "team" experience for operators), or, in order to provide a common experience for operators, require that multiple machines be mechanically ganged into a relatively large multi-user assembly and that operators assemble at a single facility for the use of such a multi-user assembly. Moreover, simulated real-time competition between such assemblies would require the co-location of multiple assemblies, typically an expensive and impractical proposition. For these and other reasons, improvements to exercise machines are desired.

Solution to Problem

Various embodiments of the disclosed apparatus and systems transcend the limitations of the prior art by enabling athletes on separate exercise machines, which may be far distant from each other, to exercise jointly in a manner that approximates the experience of exercising jointly on a real physical apparatus (e.g., rowing shell). Moreover, various embodiments of the disclosure enable athletes to train with or against simulated athletes. Some other advantages offered by embodiments of the disclosure shall be made clear hereinbelow both descriptively and with reference to the Figures.

Various embodiments replace the dissipative mechanism of the prior art with an electrical machine (generator) whose power output is dissipated largely by a resistive electrical load. Various embodiments comprise additional computational, communicative, and other aspects. In various embodiments, one or more computational aspects collect measurement information telemetrically from portions of the exercise machine; issue commands to controllable aspects of the exercise machine (e.g., electrical machine, resistive load); and communicate informatically (e.g., through a network) with various devices that can include, but are not necessarily limited to, one or more of (1) other exercise machines, (2) a server that can gather and store data pertaining to multiple exercise machines and their operators and coordinate the behaviors of multiple exercise machines, (3) other computing devices, including devices operated by one or more coaches and/or by team participants with distinctive roles (e.g., coxswains), and (4) sources of physiometric information such as wearable athletic monitors or activity trackers. The computational aspects of various embodiments include software capabilities for (1) calculating and recording the performance of teams and individual operators, (2) rating and otherwise analyzing operator and team performance, (3) algorithmically modeling combinations of one or more operators, who may be at disparate physical locations, into one or more "virtual teams" whose members' efforts affect the loads experienced by the one or more operators in a manner that simulates joint effort applied to a specific apparatus (e.g., a rowing a four-person scull), (4) numerically simulating the efforts (e.g., oarstroke timing, power, and duration) of one or more "simulated operators" and the effects of these efforts on the loads experienced by real operators and by other simulated operators, and (5) calculating the performance of combinations of real and simulated operators so that individual operators may train as part of a complete team, or a partial team may train as part of a complete team, or one virtual team (entirely real or partly or entirely simulated) may compete against one or more other teams (entirely real or partly or entirely simulated). The performance characteristics of a simulated operator constitute a set of tunable parameters that may be based on the measured characteristics of a real operator, selected from a library, custom-specified, randomly generated, or otherwise specified.

Also, various embodiments comprise devices that offer audiovisual feedback to operators that can supplement the feedback supplied by the mechanical load of the exercise machine: for example, a rowing-machine operator may face a device that gives visual and/or aural cues such as an audiovisual representation of a lead rower, the sound of a coxswain's voice (real or simulated), scenery to providing a visual indication of motion, performance metrics (e.g., stroke rate, operator power output), and the like. It may be beneficial for the audiovisual feedbacks offered to multiple operators training as a team to be coordinated by a computational device so that operators are offered consistent cues. Audiovisual feedback is in some embodiments provided to the operator by a virtual reality device (e.g., Oculus Rift) to endow the training experience with a high degree of psychophysical realism. In one example, rowers on a virtual crew team—every one of whom is hundreds of kilometers away from every other—share a virtual reality in which each operator occupies a definite point of view in a virtual watercraft, and movement of the virtual watercraft (and potentially of competing virtual watercraft) in the virtual reality is determined algorithmically from the physical efforts of the operators.

In various embodiments, the disclosed apparatus comprises an electrical machine (e.g., a linear or rotary electrical generator) that is motivated by one or more operators and supplies power to a load (e.g., a bank of resistors). Regarding the provision of load for the operator, the electrical machine and its load bank correspond approximately to the dissipative load mechanism of an exercise machine built according to the prior art. Such prior-art dissipative mechanisms include (1) piston mechanisms, whereby load is presented by hydraulic cylinders attached to handles, and (2) braked flywheel mechanisms, wherein load presented by a flywheel braked using friction pads, electromagnets, air fins, water paddles, or other dissipative contrivances. In various embodiments of the disclosure, a linear electrical machine is employed in a manner analogous to a resistive hydraulic cylinder, or a load-feeding rotary electrical machine is employed in a manner analogous to a flywheel load.

In various embodiments, the load that dissipates power generated by the electrical machine can comprise one or more resistors that dissipate energy as heat. The one or more resistors of the electrical load are herein collectively termed "the electrical load bank." In one example, the net resistance of the electrical load bank is fixed and the current through the load bank is varied in proportion to the required load. Alternatively, the net resistance of the electrical load bank is adjustable by means of signals transmitted from the system controller: e.g., relays may connect or disconnect resistors in the electrical load bank, thus increasing or decreasing the mechanical load presented to the operator. Additionally or alternatively, the electrical load bank may comprise continuously variable resistive elements (e.g., potentiometers). Non-electrical loads such as friction brakes and fluid-stirring mechanisms may be comprised by various embodiments, additionally or alternatively to resistive and other electrical loads.

In various embodiments that comprise a flywheel and a separately excited alternator as the rotary electrical machine, the flywheel is coupled by a transmission mechanism (e.g., gearbox, common axis, or sprocket and roller chain) to the rotary electrical machine, which the flywheel drives. The torque $T_{elec}$ of the alternator is determined by the mutual inductance $L_{af}$ (between the alternator's armature and field circuit, by the alternator's armature current $I_{arm}$, and by the alternator's field circuit current $I_{fld}$. An electrical load bank (resistance R) is in series with the alternator's armature circuit. Thus, $T_{elec}$, which contributes to the load encountered by the exercise-machine operator, may in such embodiments be adjusted by altering at least one of R, $I_{arm}$ and $I_{fld}$.

Additionally or alternatively in various embodiments, components of a rotary electrical machine may be weighted so as increase the electrical machine's moment of inertia, enabling the electrical machine to act as an additional flywheel or as the system's sole flywheel. Moreover, additionally or alternatively, the flywheel and/or rotary electrical machine may have a controllable moment of inertia (e.g., may incorporate devices that move mass toward or away from the axis of rotation).

Herein, the terms "user," "operator," and "athlete" are used interchangeably.

Advantageous Effects

Various embodiments of the disclosure combine load control with networked communications and model-based control of loads to transcend shortcomings of the prior art. The ability of various embodiments to combine operators at a single location or multiple locations into one or more virtual teams, each of whom experiences a varying load that realistically approximates the experience that would be had in a shared physical setting (e.g., in a boat on the water, or in a multi-user trainer with load linkage), overcomes the prior art's requirement that team members assemble at a common location to practice the coordinative aspects of their sport. Since individual machines are linked informatically, not mechanically, if all team members do assemble at a common time and place there is no need to find room for a large multi-unit assembly, as in the prior art, in order to exercise in a linked manner: in an example, rowing machines scattered about a room can operate as a multi-unit trainer.

As shall be made clearer with reference to the Figures, certain functions offered by some embodiments of the disclosure are entirely novel as compared to the prior art. In an example, in various embodiments a single operator may practice as a member of a team whose other members are all simulated. In further examples, multiple operators may, regardless of their physical locations, (1) practice together as a complete team with realistic performance/load linkage, (2) practice with a combination of real operators and simulated operators (e.g., if there are not enough real operators to form a complete team, the team complement may be filled out by simulated operators), (3) be combined variously by a user (e.g., coach) into alternative team lineups, without any need for the operators to change locations or even get off their machines, and (4) compete with real or simulated teams regardless of the location of any operators. Moreover, the physics of different phases of team effort can be simulated by appropriate manipulation of exercise machine loads (e.g., higher loads during acceleration; in rowing or biking, higher values for water and/or air resistance loads at higher velocities; in rowing or biking, higher loads when going against a current or biking uphill, respectively). In a further example, embodiments of the disclosure can both enhance training for traditional team rowing and expand the established sport of competitive indoor rowing in ways that will be clear to persons familiar with these sports.

These and other objects, along with advantages and features of the disclosure, will become more apparent through reference to the following description, the accompanying drawings, and the claims. Furthermore, it is to be understood that the features of the various embodiments described herein are not mutually exclusive and can exist in various combinations and permutations. Furthermore, the particular features, structures, routines, steps, or characteristics may be combined in any suitable manner in one or more examples of the technology. Also, although single-user trainers are frequently referenced herein, multi-user trainers may be similarly incorporated in embodiments of the disclosure. All such variations are contemplated and within the scope of the disclosure.

BRIEF DESCRIPTION OF THE FIGURES

The foregoing and other aspects of the present disclosure will become apparent to those skilled in the art to which the present disclosure relates upon reading the following description with reference to the following figures.

DESCRIPTION OF EMBODIMENTS

In the Figures and discussion thereof, systems and methods are disclosed that enable the construction of an exercise machine which improves aspects of individual and team training. These systems and methods can provide networked communication between multiple exercise machines to provide machine users with a common exercise experience that simulates aspects of joint operation of a single athletic apparatus or of operation in a common environment of separate athletic apparatuses. The types of exercise machine to which these systems and methods apply include, but are not limited to, rowing machines, stationary bicycles, elliptical machines, and cross-country skiing machines. This disclosure primarily describes illustrative cases in which the exercise machine is a rowing machine, but no restriction is intended by this usage. In the Figures, for the sake of clarity, certain features are omitted whose necessity or utility would be clear to persons familiar with the design and operation of exercise machines and other relevant devices; for example, detailed provisions for wiring an alternator or for plugging into mains power are not depicted, and force transmission mechanisms standard to various exercise machines are not depicted. The emphasis of the Figures is on features that clarify embodiments of the disclosure.

Figure 1:
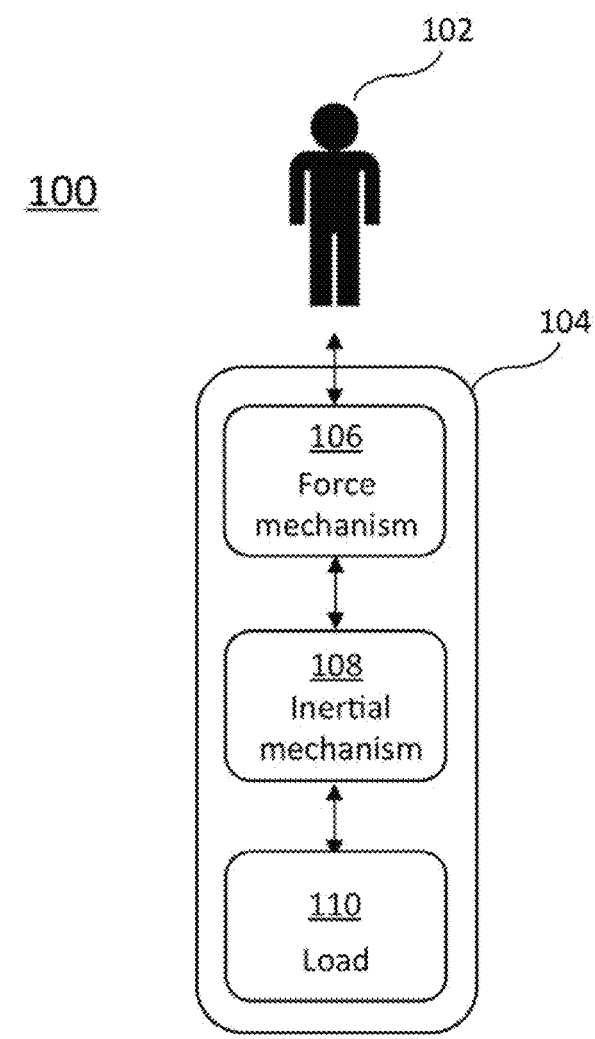
FIG. 1 is a schematic representation of a single-user exercise system according to one form of the prior art.

FIG. 1 schematically depicts portions of an illustrative single-user exercise system 100 according to one form of the prior art. A user or athlete 102 operates an exercise machine 104. The exercise machine 104 comprises a force mechanism 106, an inertial mechanism 108, and a damping mechanism or load 110. The force mechanism 106 transmits forces between the body of the athlete 102 and other portions of the exercise machine 104: in an example, in a stationary bicycle the force mechanism 106 comprises seat, handlebars, pedals, sprocket, chain, and other components. In another example, in a rowing machine the force mechanism 106 comprises seat, foot stretcher, handle, and other components. The inertial mechanism 108 typically comprises a flywheel, and smooths operation of the exercise machine by simulating the inertia of an athlete moving with a mobile athletic apparatus (e.g., cyclist on bicycle, rower on watercraft). The load 110, which is typically adjustable, simulates dissipative and possibly other loads experienced by an athlete moving an athletic apparatus (e.g., resistance of air and/or water, friction, uphill travel). The schematization or breakdown of a typical exercise system 100 shown in FIG. 1 is offered to clarify subsequent Figures and discussion, but is to some degree arbitrary, and other schematizations are possible.

Figure 2:
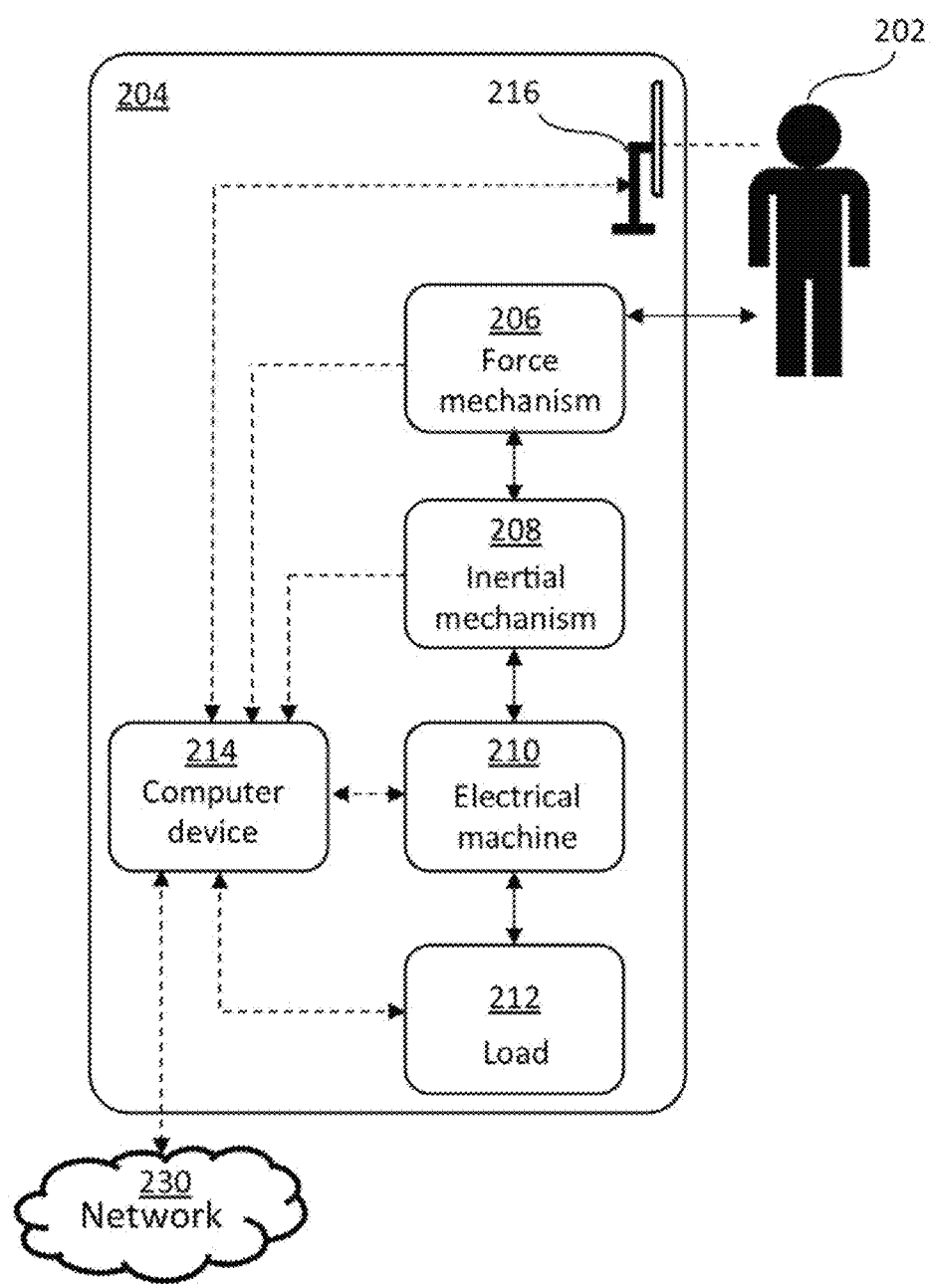
FIG. 2 is a schematic representation of an illustrative exercise system according to at least one aspect of the present disclosure.

FIG. 2 schematically depicts portions of an illustrative exercise system 200 according to an embodiment of the present disclosure. An athlete 202 operates an exercise machine 204. The exercise machine 204 comprises a force mechanism 206, an inertial mechanism 208, an electrical machine 210 (e.g., linear or rotary generator), a damping mechanism or load 212, a computer device 214, and a user interface device 216. In various embodiments, the electrical machine 210 can be any suitable device including, but not limited to, a separately excited electric machine, alternating current induction motor, permanent-magnet alternating current motor, or brushed or brushless direct current motor. The force mechanism 206 transmits forces between the body of the athlete 202 and other portions of the exercise machine 204. The inertial mechanism 208 can comprise a flywheel. The electrical machine 210 is coupled to the inertial mechanism 208 by a transmission mechanism (not shown) and constitutes a mechanical load on the inertial mechanism 208. In various embodiments, the inertial mechanism 208 and electrical machine 210 are integrated into a single device (e.g., a rotary electrical machine with an appropriately high moment of inertia).

The load 212 comprises an electrical load which serves to dissipate or absorb electrical energy produced by the electrical machine 210. In one example, the electrical load is adjustable in magnitude. In various embodiments, the load 212 comprises resistors, a battery, an AC/DC converter and/or a DC/DC converter, and various electrically powered components of the exercise machine 204 or of other devices.

The user interface 216 comprises one or more of audio, visual, and tactile means of conveying information to the athlete 202, where such information can comprise metrics of athlete performance (e.g., stroke rate, power output), athlete biometrics (e.g., heart rate), audiovisual representations or simulations (e.g., virtual reality), audio (e.g., voice, rhythm cues), and others. The user interface 216 also comprises one or more means of information input from the athlete 202 (e.g., voice input, keyboard input, touchscreen input, eye-movement based interaction, etc.).

The computer 214 comprises a data-gathering capability, computational capability, control capability, communications capability, and memory capability. The data-gathering capability of the computer 214 receives signals from sensors (not shown) communicating with various portions of the exercise machine 204. In FIG. 2, dashed arrows denote informatic transmission paths (as distinguished from mechanical and electrical energetic transmission paths, denoted by solid arrows). Thus, the computer 214 receives sensed information from and transmits (via its control capability) controlling commands to the force mechanism 206, inertial mechanism 208, electrical machine 210, load 212, and interface 216. The control capability of the computer 214 enables it to command changes in the states of various components of the exercise machine 204. For example, the computer 214 may transmit signals that cause the excitation current in a winding of the electrical machine 210 to increase or decrease, thus altering the torque placed by the electrical machine 210 on the inertial mechanism 208 and ultimately altering the mechanical load felt by the athlete 202. In another example, the computer 214 transmits signals that cause a resistive component of the load 212 to increase or decrease, altering the load on the electrical machine 210 and ultimately altering the mechanical load felt by the athlete 202.

The communications capability of the computer 214 enables it to exchange information with a network 230. The communications capability is capable of information exchange through one or more wired channels and protocols, one or more wireless channels and protocols, or both. In an example, the network 230 comprises a number of exercise machines that are similar to exercise machine 204 and are interconnected by cabled or wireless channels, where machine 204 and the machines with which it is in communication act as communicative nodes in a network topology. In another example, the network 230 is the internet. Through the network 230, the computer 214 can be in informatic communication with machines similar to exercise machine 204, general computing devices, and other devices capable of informatic exchange through the network 230. In an example, the exercise machine 204 communicates through the network 230 with a wearable sensor device worn by the athlete, acquiring biometric information (e.g., heart rate) and utilizing such information in the computation and memory capabilities of the computer 214.

The exercise machine 204 can be in communication via the network 230 with M−1 other, similar exercise machines (best represented in FIG. 4A), which are typically also in communication with each other. Together, the exercise machine 204 and the M−1 exercise machines with which it is in networked communication constitute a networked group of M exercise machines. The quantity of members of a networked group may vary from occasion to occasion.

As shall be made clear with reference to illustrative embodiments hereinbelow, the computational capability of the computer 214 implements a computational algorithm, herein termed the "team algorithm." The team algorithm accepts as numerical inputs measured electrical and mechanical quantities from portions of the machine 204 (e.g., rotational velocity of a flywheel, acceleration of a flywheel, voltage across a resistive load, current in a generator winding). These measured quantities are such as enable estimation of the real-time effort exerted by the athlete 202 and, potentially, of other quantities. The team algorithm also accepts as inputs a number of numerical parameters stored in the memory capability of the computer 214. These parameters can express physical properties of a hypothetical apparatus (e.g., a particular type of watercraft), physical characteristics of a given exercise machine (e.g., the moment of inertia of a flywheel), physical characteristics of athletes (e.g., mass), and other variables. The team algorithm can also accept as input real-time data representing the activities of N athletes, N≥1, one of whom may be the operator 202 of the exercise machine 204. The N athletes whose activity data are inputted to the team algorithm are herein said to constitute a "virtual team." Activity data may be derived from the activities of real human athletes, or numerically generated, or both: that is, some or all of the N networked athletes on a virtual team may be real athletes and some or all may be simulated athletes. Simulation of an athlete is performed by code computed by the computer 214 or by some computer device with which computer 214 is in communication via the network 230. Simulation can be based on parameters derived by measurement from real athletes or otherwise derived, and may include a random aspect (e.g., the efforts of a simulated rower may vary slightly in a realistically nondeterministic fashion from stroke to stroke). If M real athletes on M real machines are participating in an N-member virtual team, then N−M team members are simulated.

Data received by the computer 214 via the network 230 during computation of the team algorithm typically include real-time data on the activities of the M−1 real athletes other than the real local athlete 202 on the virtual team. Real-time data on the activities of the real local athlete 202 are gathered directly by the computer 214 from machine 204. Also, the computer 214 typically transmits activity data on the local athlete 202 via the network 230 to the M−1 machines from which the machine 204 is receiving athlete activity data. Data on the activity of simulated athletes on a virtual team may be produced locally by the computer devices of exercise machines (e.g., computer 214), or communicated to or among exercise machines or computers via the network 230, or both.

The team algorithm computed by computer 214 produces commands that are communicated to various controllable mechanisms of the machine 204 (e.g., aspects of the electrical machine 210 and load 212), ultimately altering the mechanical load experienced by the athlete 202. The M−1 other networked machines similarly compute the team algorithm to calculate commands for their own mechanisms, thus affecting the experiences of their own operators in a manner coordinated with that of machine 204. That is, the M machines of the M real athletes on an N-member virtual team all possess or receive activity information for N athletes and compute load adjustments for the N athletes. For the M machines of the virtual team operated by real athletes, physical load adjustments are actually made; for the N−M simulated athletes, adjustments can be made to the simulation calculations, appropriately altering the effort data corresponding to each simulated athlete. The method of measurement, calculation, and apparatus adjustment herein described constitutes a form of closed-loop control.

The team algorithm, operating on real activity data from M real athletes and simulated activity data from N−M simulated athletes, and consequently modifying the loads specified for both real and simulated athletes on an N-member team, is designed to approximate the performance of an actual athletic apparatus (e.g., rowboat) operated jointly by the N team members. By altering the parameters of the team algorithm, the physical responses of various apparatuses may be simulated (e.g., 4-rower craft of a first type, 4-rower craft of a second type, 8-rower craft). Real athletes participating in a virtual team experience time-varying resistance from their exercise machines that reflects the efforts of other team members, real and simulated, in a manner approximating joint team operation of a real physical apparatus, even though other real team members are operating physically separate machines that may be geographically distant. In an example, the exercise machine 204 is a rowing machine and the athlete 202 is a rower participating in a virtual team rowing a virtual four-person scull. The resistance presented by the handle or oar to athlete 202 will vary throughout each stroke and from stroke to stroke in a manner that depends via the team algorithm on the timing, power, and other features of the strokes of athlete 202, on the strokes of the other three athletes on the team, and on the characteristics of the watercraft model chosen as the virtual apparatus (e.g., four-person scull).

Moreover, the outputs of the operator interface 216 are typically altered in coordination with team performance as determined by the team algorithm. In an example, the interface 216 comprises a virtual-reality headset, the virtual apparatus simulated is a four-rower watercraft, a participating athlete 202 experiences a visual field with coordinated audio placing them in a specific position in the virtual watercraft in a given water environment, and the watercraft is seen by the athlete 202 to move through its environment in a manner dependent on the team's joint efforts. One or more competing virtual watercraft may be represented in the perceived environment, either simulated or partly or wholly rowed by real athletes, and real competing athletes may be supplied with complementary points of view in the virtual reality. Quantitative data on individual performance, team performance, competitor performance, and other variables can be made selectively available (e.g., visually) to individual athletes, coaches, teams, and others. Audio, video, and other data gathered from athletes and other parties (e.g., coaches, onlookers) may be integrated variously with the outputs of the operator interface 216 to produce virtual settings of varying character, interactivity, and realism, enabling the training of athletes in the psychosocial as well as physical aspects of a sport. Sport onlookers may be linked to the system through virtual-reality headsets, enabling audiences to be virtually present at virtual races rowed by real and/or simulated athletes, where all onlookers and real participants may be separated geographically to any degree. Other forms of interface coordination, e.g., coach audio shared simultaneously to all athletes on a virtual team, are also contemplated and within the scope of the disclosure. All such applications, however elaborate, depend on the capability of various embodiments of the disclosure to mechanically produce for each individual exercise-machine user an exercise experience that reflects both that machine user's efforts and the simultaneous efforts of other users, real and/or simulated.

It is possible to apply the described apparatus and methods to other types of exercise machines. In an example, the exercise machine 204 of FIG. 2 is a stationary bicycle that can simulate real-world load conditions of various topographies, drafting effects from different locations in a riding pack, tandem riding, etc., whether for a single rider or simultaneously for members of a team using a networked group of similar exercise machines. In another example, the exercise machine 204 is a cross-country ski machine that can simulate various topographies, wind conditions, snow types, etc. In general, any suitable type of exercise machine can employ the described apparatus and methods to enhance group workouts and to enable the use of customized, possibly time-varying load profiles for individual workouts.

Figure 3:
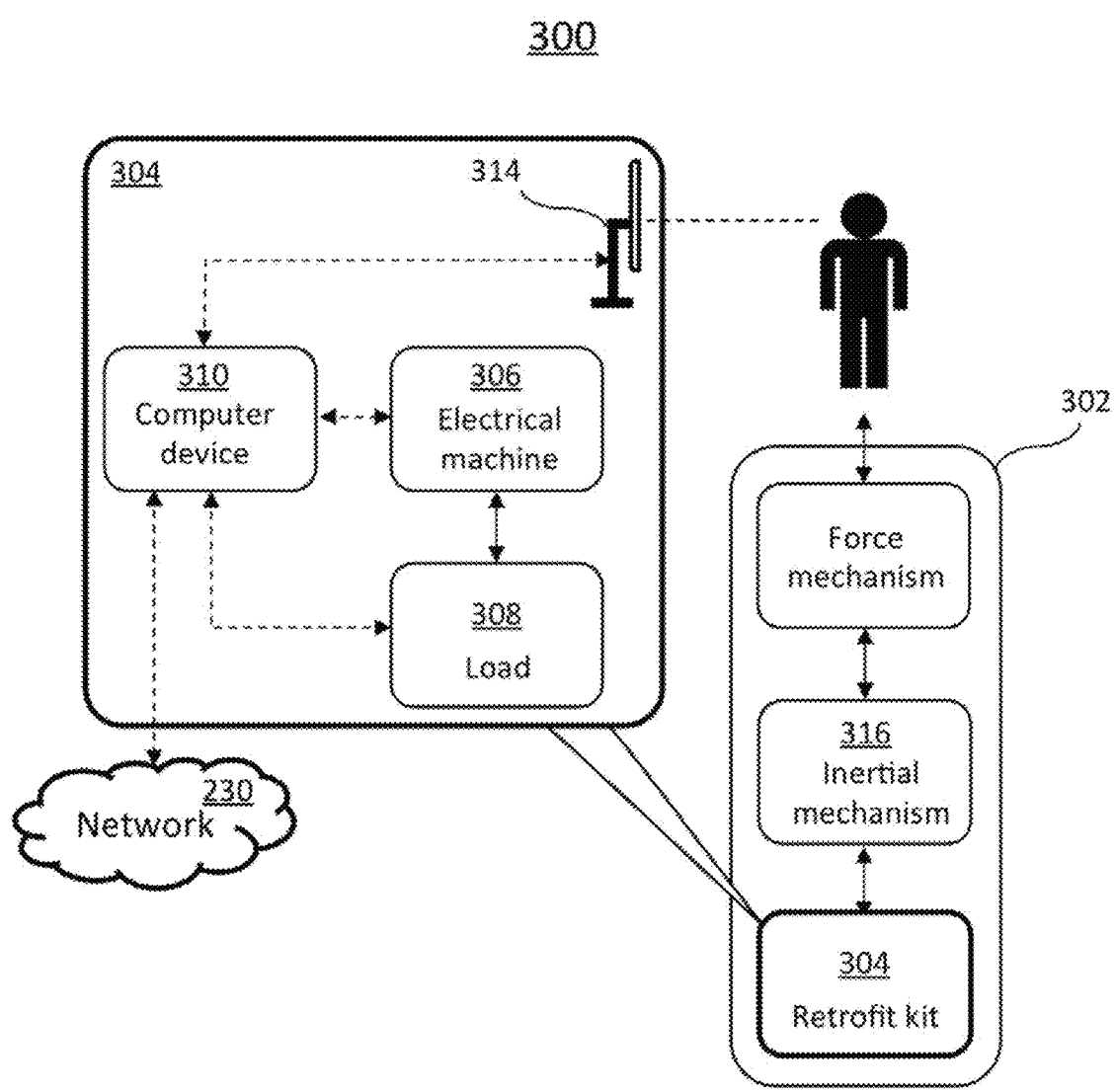
FIG. 3 is a schematic representation of at least one embodiment of the present disclosure showing the addition of a retrofit kit to the exercise system of FIG. 1 for conversion to the exercise system of FIG. 2.

The advantages of embodiments of the disclosure may, in some instances, be realized by modifying or retrofitting an existing exercise machine built according to the prior art. FIG. 3 depicts the retrofitting of an exercise machine 302 built according to the prior art with an illustrative "retrofit kit" 304. The machine 302 is, before retrofit, similar to the machine 104 of FIG. 1. The load mechanism of the prior-art machine 302, corresponding to the load mechanism 110 of machine 104 of FIG. 1, is removed and replaced by the retrofit kit 304, which comprises an electrical machine 306, load 308, computer 310 capable of communicating with a network 230, and an operator interface 314. The properties of the electrical machine 306, load 308, computer 310, and interface 314 are as described above with reference to corresponding components in FIG. 2. For retrofit to occur, an appropriate transmission mechanism (not shown) must in general exist or be provided (e.g., as part of the kit) for linking the inertial mechanism 316 of the machine 302 to the electrical machine 306 of the kit 304. In an example, the inertial mechanism of a rowing machine comprises a flywheel, the electrical machine 306 of the retrofit kit 304 comprises a rotary electrical generator, and with appropriate attachment hardware, a sprocket-and-chain transmission can be employed to link the flywheel to the generator.

Figure 4A:
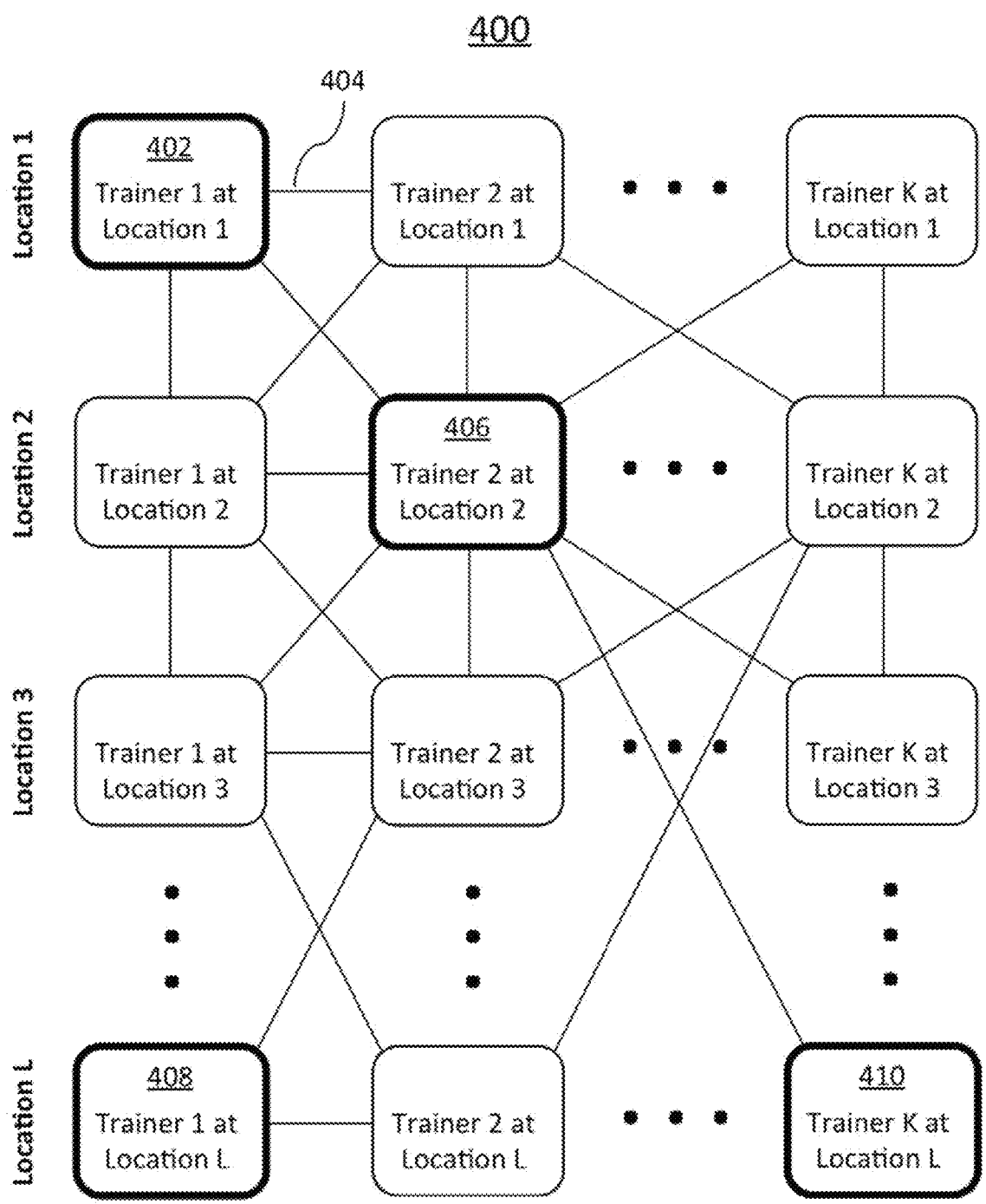
FIG. 4A is a schematic representation of an exemplary decentralized network comprising a number of exercise systems, each similar to the exercise system of FIG. 2.

Reference is now made to FIG. 4A, which schematically depicts an illustrative network 400 comprising a number of exercise machines (e.g., trainer 402), each similar to the exercise machine 204 of FIG. 2. For simplicity, the network 400 comprises L physical locations (e.g., gymnasia), each with K trainers (total N=L×K trainers), each trainer potentially accommodating a single athlete. Ellipses indicate trainers not explicitly depicted. In the topology of FIG. 4A, communication pathways (e.g., pathway 404) enable each trainer to communicate with at least one additional trainer. It is to be understood that FIG. 4A shows a limited number of exercise machine communication pathways for the sake of clarity, but that in general each trainer in the network can be connected to every other; further, it is a well-known mathematical result that the total number of possible communication pathways (one node direct to another) in such an arrangement is $N(N-1)/2$. In the illustrative network topology of FIG. 4A, software running on the computational capabilities of the individual trainers enables the trainers to communicate with each other and thus for the operators of various trainers to associate with each other in one or more teams. For example, in FIG. 4A, the operators (e.g., athletes or rowers) of trainers 402, 406, 408, and 410 (highlighted by heavier outlines) have associated into a four-member team. All four team members can now work out simultaneously on a common virtual apparatus (e.g., four-person scull); the load experienced by each team member will be adjusted in real time, as a function of the efforts of all team members and the chosen load profile of the virtual apparatus, to approximate the sensation of engaging with a jointly operated physical apparatus. The network 400 may also be referred to as a simulation system or a crew training simulation system.

Figure 4B:
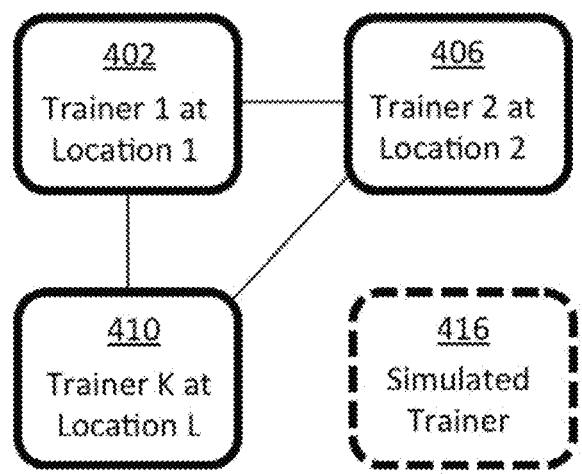
FIG. 4B is a schematic representation of an example four-member team in the network of FIG. 4A.

FIG. 4B depicts another example of a four-member team 414 in the network 400 (best seen in FIG. 4A), for clarity showing only the trainers of team members and the communications pathways connecting them. Team 414 consists of the operators of trainers 402, 406, 410, and the virtual operator of a simulated operator trainer 416. The activity data of simulated trainer 416 can be calculated locally (i.e., redundantly) by the computational capabilities of all three trainers 402, 406, 410 or can be calculated by any one of the trainers 402, 406, 410 and communicated to the other two.

Figure 5:
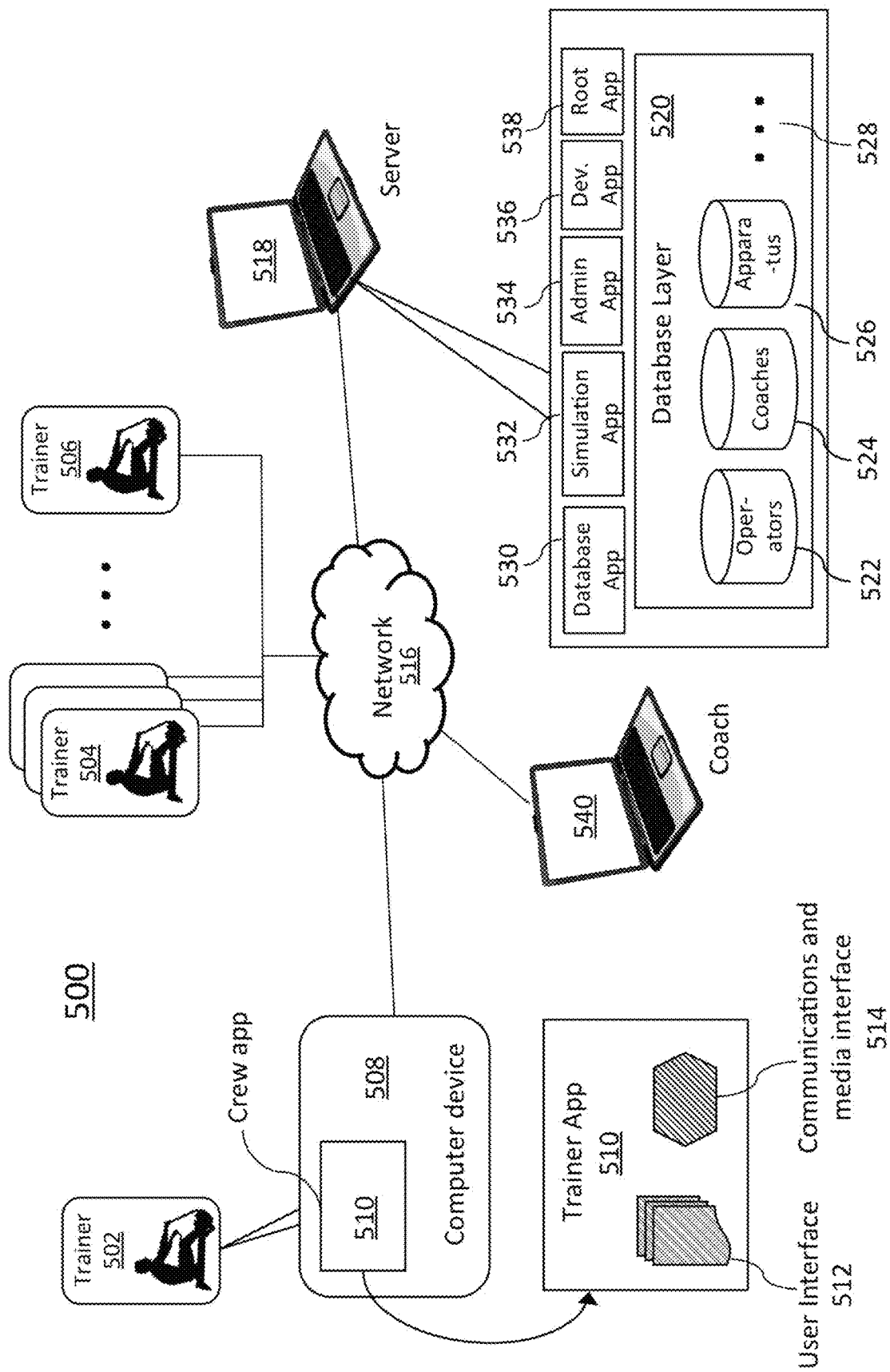
FIG. 5 is schematic representation of an exemplary centralized network comprising a number of exercise systems, each similar to the exercise system of FIG. 2.

Another illustrative embodiment of a network with additional details and having a topology that differs from that of FIGS. 4A and 4B, is schematically depicted in FIG. 5. The illustrative topology of FIGS. 4A and 4B is decentralized, whereas the illustrative topology of FIG. 5 is centralized: additional architectures will be readily envisaged by persons familiar with the art of device networking and control, and all such architectures are contemplated and within the scope of the disclosure. The embodiment of FIG. 5 comprises a crew training simulation system 500. The system 500 comprises some number N of trainers with associated real operators, e.g., trainers 502, 504, 506. Ellipses indicate trainers not explicitly depicted. Trainer 502 is typical of the trainers comprised by the system 500. The computer device 508 of trainer 502 runs a program (application, app) 510 termed the Crew App. The program 510 implements the team algorithm (not shown), a user interface 512 that governs interactions with the operator of the trainer 502, a communications and media interface 514 that handles interactions with the network 516 (which corresponds to the network 230 of FIG. 2), and other functions. In the illustrative system 500 of FIG. 5, the network 516 is the internet and the computer device 508 communicates with the network 516 via a standard wireless technology (e.g., WiFi, Bluetooth). The various trainers (e.g., trainers 504, 506) communicate independently and simultaneously with the network 516; the number N of trainers connected to the network 516 typically increases and decreases over time as trainers are logged in and out of the system 500. In one example, only trainers occupied by operators will be logged in, i.e., in active communication with the network 516. The trainers may communicate directly with each other through the network 516, or may communicate with each other solely or primarily through the agency of a server 518, which is also in communication with the network 516. The server 518 can be a computing device (e.g., laptop, desktop, tablet) capable of overseeing coordination of trainers, communications between trainers and operators, simulation of team operation of virtual apparatuses, other simulation tasks (e.g., virtual reality generation), and storage, retrieval, and generation of data pertaining to the operation of the system 500 (e.g., data pertaining the conduct of simulated training runs and competitions). In various embodiments, the server 518 is not a unitary computing device (e.g., laptop computer); that is, its computational and data-storage capabilities may be realized by multiple devices, either redundantly or in a distributed (e.g., cloud-computing) manner, where such multiple devices may include the computer devices comprised by the trainers. Thus, no restriction is intended by the representation of the server 518 as a unitary device in FIG. 5. The server 518 comprises a database layer 520 that implements access to one or more databases, e.g., an operators database 522 (recording information pertaining to individual operators, both real and simulated), a coaches database 524 (recording information pertaining to coaches or other coordinative system users), an apparatus database 526 (containing information pertaining to virtual apparatuses), and potentially other databases 528, indicated in FIG. 5 by ellipses, which may contain any data deemed pertinent to the conduct of the system 500 (e.g., measured mechanical characteristics of individual trainers, outcomes and statistics pertaining to simulated races).

The server 518 comprises software programs that implement various functional aspects of the system 500. These programs can include a database app 530, which maintains the contents of the database layer 520 and retrieves information for serving to trainers and other devices as needed; a simulation app 532, which calculates the team algorithm, calculates the activities of simulated operators, and performs other calculative tasks; an administrative app 534, which enables a master user to act at an operations management level; a developer app 536, which enables access to the application programming interfaces of the system for application development; and a root app 538, which enables master control over other user categories and access to everything contained in the database layer 520. In various embodiments, the functions realized in the illustrative system 500 by the database layer 520 and the apps 530, 532, 534, 536, and 538 are realized by a differently organized set of applications or software modules. Moreover, the system 500 can comprise one or more additional computing devices, e.g., a coach device 540 supplying authorized access to a "coach," i.e., user having coordinative, administrative, or oversight powers. The coach device 540 may in various embodiments or modes of operation of system 500 be the computer device of one of the trainers (e.g., trainer 502), a laptop or desktop, or a mobile computing device. The network 516 may also communicate with other networks and with devices connected thereto.

In an illustrative mode of operation of system 500, a coach device 540, communicating with the server 518, is authorized to work with some subset of the N trainers logged on to the system 500. For example, the coach device 540 may be one of a limited number of coach devices at a university authorized to access the system 500 as part of a paid subscription service. The user of coach device 540, employing a software capability running on their computer device, chooses the operators of P trainers, a subset of the N trainers, to be members of a virtual team. The user of the coach device 540 also specifies a specific virtual apparatus and, potentially, other conditions that will influence the load profile of the run (e.g., race topology, wind conditions, race duration). The server 518 sets up a computational model (e.g., team algorithm) with parameters set and/or updated during simulation to reflect the choices transmitted by the coach device 540 and other pertinent variables (e.g., trainer-specific mechanical characteristics) and employing also as inputs activity data from the P team members. The run begins on a signal from the coach device 540 or at a set time, whereupon activity data from the P trainers begins to be transmitted to the server 518 through the network 516. The server 518 computationally models the behavior of the virtual apparatus based on its various parameters and the activity data received and transmits instructions for each of the P trainers accordingly to modify the loads experienced by the trainer operators (e.g., by increasing or decreasing the current to a generator winding). The run terminates at another signal or time. The server 518 records in its database layer 520 all data received or generated by the server 518 during the course of the run, which may include activity data from the trainers, operators' physiometric data that may have been transmitted through the network 516 from activity monitors, race outcomes, and the like.

The topology of FIG. 5 requires on the order of N communicative channels, as opposed to the N(N−1)/2 channels of the topology of FIG. 4.

The number of distinct virtual teams that can be assembled using either the topology of FIG. 4A or of FIG. 5 grows rapidly with N. By the binomial theorem, the number of possible teams of size P that can be specified from N operators without regard to order (i.e., the number of combinations of size P) is given by the binomial coefficient, N!/(P!(N−P)!). However, in many sports team-member ordering does matter (e.g., it matters where crew members are seated in a boat); in such sports, the number of teams of size P that can be specified from N operators with regard to order (i.e., number of permutations of size P) is $N^P$. Thus, embodiments of the disclosure enable athletes, including both athletes at a single facility and athletes at widely separated facilities, to be rapidly and easily combined and recombined in a potentially very large number of virtual teams of various sizes, exercising on virtual apparatuses and in virtual environments of practically unlimited number. This capability is not offered in practicable form by the prior art (which requires athletes to assemble at a common location to practice as a team, and to jointly operate large multi-user training apparatuses, or actual athletic apparatuses in the field, to train as a team). The combinatoric team-forming capability of embodiments of the disclosure offers many advantages: e.g., a coach can easily try out a number of team permutations to see which is the most competitive under specified environmental conditions, using specified athletic apparatuses, and so on.

In another illustrative mode of operation of system 500, more than one virtual team may be assembled at a time, by one or more coaches, from among the N available trainers (assuming sufficiently large N) and set to compete against each other in a virtual race. The simulation of each team's run may occur independently of the simulation of each other team's run, or the simulation app 532 may comprise provisions for modeling interactions of teams in a virtual environment.

In yet another illustrative mode of operation of system 500, one or more team members of one or more virtual teams may be simulated by the server 518. At one extreme, all participating athletes are real and no simulated athletes are employed; in various mixed cases, one or more real athletes and one or more simulated athletes are employed; and at another extreme, all athletes are simulated. The latter mode of operation of system 500 may be used for training of coaches, for investigation of various styles of team formation and competition tactics, and other purposes.

Figure 6A:
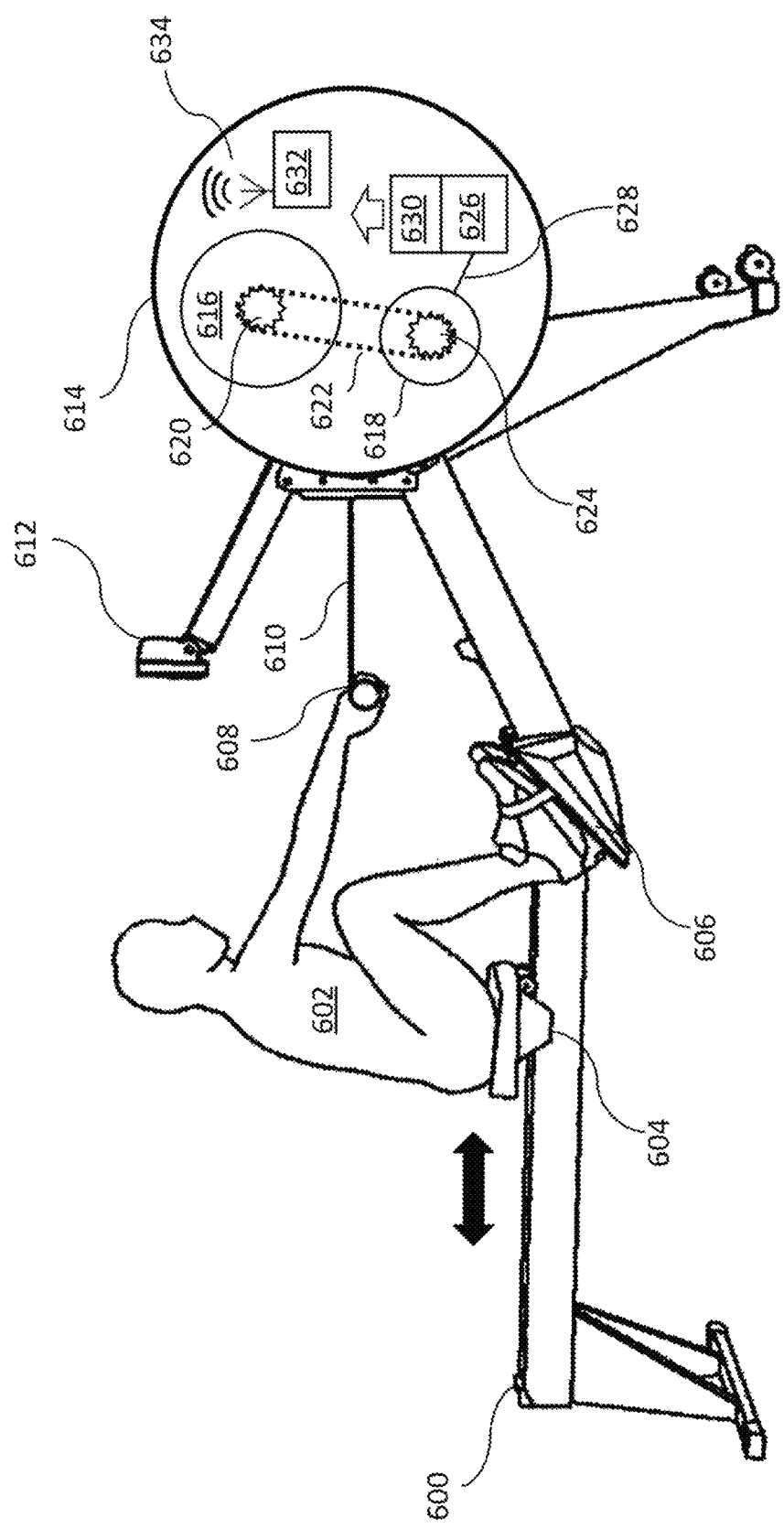
FIG. 6A is a side view of an example exercise system of FIG. 2.

FIG. 6A schematically depicts in side view portions of an illustrative embodiment of the disclosure comprising a rowing machine 600. The rowing machine 600 is operated by a rower 602 and comprises a sliding seat 604, a foot stretcher (brace) 606, a handle 608, a connective structure 610 (only partly depicted), a user interface device 612, and a protective housing 614. The rowing machine 600 also comprises, inside the protective housing 614, a flywheel 616, a generator 618, a first sprocket 620 attached to the flywheel 616, a loop chain 622, a second sprocket 624 attached to the generator 618, an electrical load bank 626, wiring 628 conveying electrical power from the generator 618 to the electrical load bank 626, a fan 630 that cools the electrical load bank 626, and a computer device (controller) 632. The controller 632 is equipped with a wireless communication capability 634 (e.g., WiFi or Bluetooth) that enables the controller 632 to communicate, through a network (best seen in FIG. 5) with other devices (best seen in FIG. 5), e.g., rowing machines similar to machine 600 or various computing devices connected to the network, such as a server. The handle 608 and connective structure 610 (a pullable cord or chain) communicate via a standard force-transferring mechanism (not shown) with the flywheel 616, enabling a force generated by the rower 602 to urge the motion of the flywheel 616 (i.e., during performance of an oarstroke). That is, the rower 602, by pulling on the handle 608, applies a torque $T_{athlete}$ to the flywheel 616. The resistance of the flywheel 616 to acceleration is determined by its moment of inertia and by any retarding torque applied to the flywheel 616, e.g., torque applied via the sprocket 620. Thus, for example, the electrical generator 618 communicates a torque load to the flywheel via sprocket 624, chain 622, and sprocket 620, increasing the resistance to acceleration of the flywheel 616. Increased resistance to acceleration of the flywheel 616 is felt by the rower 602 as increased pulling resistance.

The rowing machine 600 is illustrative: other configurations, which will be known to persons having skill in the art, are possible. In the illustrative embodiment of FIG. 6A, the generator 618 is an alternator. Various sensors, wires, and other components of the machine 600 are not depicted in FIG. 6A for the sake of clarity.

Referring again to FIG. 6A, one particular example of the exercise machine 600 can be a rowing machine as described above. The exercise machine 600 includes a cyclical actuator 608, which can be a handle. In one example, the handle can be configured to replicate a handle of an oar used on a typical watercraft, such as a multi-rower shell. The cyclical actuator 608 is movably mounted to the exercise machine 600.

Referring again to FIG. 6A, an illustrative example of an exercise machine according to this disclosure can be a rowing machine 600 as described above. Components corresponding to some parts of the illustrative machine 600 can be comprised by exercise machines according to various other embodiments of the disclosure as follows. The handle 608 of FIG. 6A can be generally understood as a cyclical actuator, which can take various forms in various embodiments. In one example, a cyclic actuator is configured to replicate a handle of an oar used on a typical watercraft, such as a multi-rower shell. In general, the cyclical actuator is movably coupled via a connective structure to the exercise machine (e.g., rowing machine 600).

Various exercise machines according to the disclosure include mechanical energy storage devices, e.g., flywheel 616 of machine 600. (Mechanical energy is stored in all moving components of an exercise system, including the athlete, but herein the phrase "mechanical energy storage device" refers to a device whose primary function is to store mechanical energy.) In the example of FIG. 6A, the mechanical energy storage device is the flywheel 616 mounted to the exercise machine 600: the connective structure 610 (cord) operatively connects the cyclical actuator 608 (handle) to the mechanical energy storage device 616 (flywheel).

It is to be understood that the mechanical energy storage device can include structures other than the flywheel 616. For example, a motor that has sufficient inertia may act as both the flywheel 616 and the electrical generator 618. Other mechanical energy storage devices are also contemplated.

In various embodiments, this relationship of parts (cyclic actuator, connective structure, mechanical energy storage device) can be realized by various mechanisms. In an example, any suitable connective structure can be used (e.g., strap, cord, chain, lever, friction wheel, pedal crank arm) that provides a physical connection between the cyclical actuator (e.g., handle, pedal, ski) and the mechanical energy storage device (e.g., flywheel, spring, moveable weight, moving fluid). In one example, a connective structure can be configured to be actuated like an oar on a watercraft. In another example, a connective structure can be placed directly in front of the operator and pulled rearward as shown in FIG. 6A. Other examples of connective structures include multiple components and combinations of components such as gears, shafts, axles, jointed rods, etc. Regardless of the physical make-up of the connective structure, the connective structure transfers and/or transforms a force generated by an operator of the exercise machine in such a manner that motion of the cyclical actuator urges motion of the mechanical energy storage device (e.g., rotation of a flywheel).

In an illustrative class of rowing machines according to some embodiments of the invention, the connective structure includes an upper axle. The upper axle can be operably connected to the cyclic actuator (i.e., handle) directly or via portions of a connective structure such that the rowing action of an operator urges the upper axle to rotate. The upper axle is mounted to the flywheel such that rotation of the upper axle urges the flywheel to rotate. A transmission mechanism connects the flywheel to a lower axle connected to an electrical generator. The individual components of the handle, the connective structure, the flywheel, the two axles, and the transmission mechanism coupling the two axles can be collectively thought of as a drivetrain to transmit motion from the operator to an electrical generator. In this example and in various other embodiments, the electrical generator 618 can be any suitable device including, but not limited to, a separately excited electric machine (SEPEX), alternating current (AC) induction, permanent-magnet alternating current (PMAC), brushless direct current motor (BLDC), etc. Additionally, the described components are but one example of a drivetrain, and any suitable means of transferring motion can be employed by exercise machines according to various embodiments of the disclosure.

Continuing discussion of the foregoing example, an exercise machine (e.g., machine 600 of FIG. 6A) in the illustrative class of machines exercise machine comprises an electrical generator 618 having a rotatable shaft that is connected to the lower axle. The rotatable shaft of the electrical generator 618 is the lower axle. The electrical generator is operatively connected to the flywheel 616 through the drivetrain such that rotation of the upper axle and/or the flywheel 616 urges rotation of the rotatable shaft in the electrical generator 618. Rotation of the motor on the generator shaft creates an electrical signal. In some members of the illustrative class of machines, the electrical generator 618 is an alternator which creates an electrical signal that is AC, which can be converted to a direct current (DC). It is to be noted that any suitable electrical generator can be used in various embodiments comprising an electrical machine. Also, exercise machines in the illustrative class of machines according to various embodiments can include a converter (e.g., a rectifier) in electrical communication with the electrical generator 618 and a resistive load bank 626. In one example, the converter converts the AC electrical signal delivered from the alternator to DC electrical signal that is passed to the electrical load bank. In other members of the illustrative class, the converter can be integral to the alternator such that the alternator delivers a DC electrical signal output.

In an exemplary member of the illustrative class, the resistive load bank 626 is configured to supplement the load resistance of the flywheel 616. The resistive load bank 626 is in electrical communication with the electrical generator 618. The resistive load bank 626 can be considered part of the "armature circuit." In another exemplary member of the illustrative class of machines, a wire harness delivers the electrical signal from the electrical generator 618 to the electrical load bank 626 and the electrical signal is dissipated at the electrical load bank 626, typically by generating heat. In one example, heat generated in the electrical load bank 626 can be dissipated using at least one fan 630. The rate of fan speed can be proportional to the average electrical load through the electrical load bank 626.

Additionally, the electrical load bank 626 can comprise various different structures to achieve the goal of dissipating the electrical energy created by physical work by the rower 602 input into the electrical generator 618. In one example, the electrical load bank 626 can comprise a series of resistors that dissipate at least a portion of the electrical signal created by the electrical generator 618. In another example, the electrical load bank 626 can comprise a combination of resistance elements and capacitance elements. In yet another example, the electrical load bank 626 can comprise thermo-electric generators. The thermo-electric generators can beneficially decrease the overall size of the electrical load bank 626 and provide electrical cooling to the electrical load bank 626.

Figure 6B:
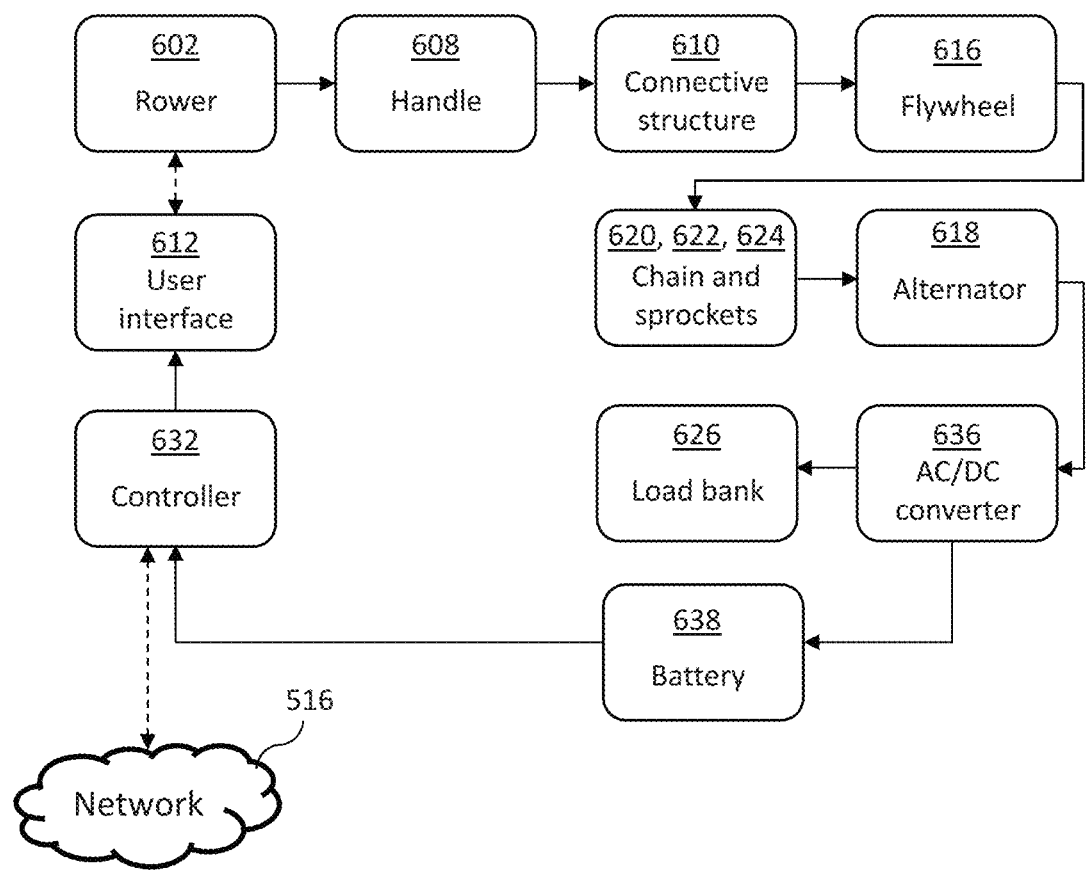
FIG. 6B is a schematic representation of the exercise system of FIG. 6A including additional components.

The operative organization of rowing machine 600, which is typical of a number of rowing machines according to various embodiments of the disclosure, is schematically clarified in FIG. 6B, with the omission for clarity of control pathways from the controller 632 to the alternator 618, load bank 626, and other components, and with the addition of several components comprised by various embodiments but not depicted in FIG. 6A. In particular, as shown in FIG. 6B the power output of the alternator 618 may be passed through an electrical converter 636. The electrical converter 636 can include an AC/DC converter and/or a DC/DC converter, and the resulting DC power may be dissipated in the load bank 626 and/or used to charge a battery 638 (e.g., a twelve-volt, sealed-lead-acid battery or a fifteen-volt lithium-ion battery), here understood to comprise an appropriate charging mechanism, which may in turn supply power to the controller 632, the user interface or display device 612, one or more windings of the alternator 618, and possibly other devices. By means of the electrical converter 636 and battery 638, the rowing machine 600 may be made self-powering as regards its electrical devices. In various embodiments, the electrical converter 636 can be integral to the alternator 618 such that the alternator 618 delivers a DC electrical output signal. For simplicity, the illustrative exercise machine 600 shown in FIG. 6A does not comprise a converter 636 or battery 638.

Referring again to the illustrative machine 600 of FIG. 6A, provisions are made (but, for clarity, not depicted in FIG. 6A) for acquiring measurement data of a number of operative variables of the exercise machine 600, to be more particularly described below. These data are conveyed (e.g., by wiring) to the controller 632, which can use these data in cooperation with various tunable parameters and a team algorithm stored in a memory capability to compute the team algorithm. The outputs of the team algorithm are used by the controller 632 to alter the load experienced by the rower 602, as shall be described. For example, as the rower 602 pulls the handle 608, this action moves the flywheel 616, which in turn rotates the alternator 618 to create an electrical signal that is dissipated by the load bank 626. The algorithm calculated by the controller 632 can be used to simulate real-world conditions of various rowing apparatuses including, but not limited to, a one-person scull, two-person scull, four-person scull, two-person sweep, four-person sweep, and eight-person sweep.

Discussion hereinbelow will first focus on the provision of a specific load profile to a user of isolated machine 600, that is, on a state of operation not incorporating activity data from other trainers or from simulated operators. Although this discussion refers for the sake of specificity and clarity to machine 600 of FIG. 6A, it will be clear to persons familiar with the science of engineering that the principles thus clarified will, with appropriate adjustments, apply equally to various other embodiments.

First, it is to be noted that the effort produced by the rower 602 at any moment can be characterized by the instantaneous torque $T_{athlete}$ exerted by the rower 602 on the flywheel 616 via the connective structure 610. The torque $T_{athlete}$ may be considered under two aspects, i.e., actual or measured $T_{athlete}$ and targeted or desired $T_{load}$. Actual $T_{athlete}$ is produced by the rower 602; targeted $T_{load}$ is a numerically calculated quantity which the exercise machine 600 will, in typical operation, proceed to produce in response to a changing state of the exercise machine 600. In general, the goal of a rower is to row at a certain rate (which, in a team context, is ideally synchronous with the rowing of team-mates): e.g., to produce a certain rate of acceleration, as during startup, or to maintain a certain speed, as during a cruising phase. Also, in the exercise machine 600, the rotational velocity ω of the flywheel 616 is analogous to watercraft speed: i.e., the angular momentum of the flywheel 616 turning at a given ω is analogous to the linear momentum of a crew-bearing watercraft moving at a given velocity. Similarly, the effort ($T_{athlete}$) required to increase or maintain the rotational velocity ω of the flywheel 616 is determined by the moment of inertia J of the flywheel 616 and by any torque loads on the flywheel 616, and this effort is analogous to that required to increase or maintain the velocity of a watercraft, which is determined by the inertia of the watercraft and crew and by any fluid drag on the watercraft. The function of the controller 632 can, in this context, be stated as follows: To require of the rower 602, as the rower 602 seeks to maintain a certain power output, an actual $T_{load}$ that matches a calculated, target $T_{load}$ reflecting hypothetical physical conditions. These hypothetical physical conditions are determined by a hypothetical apparatus (e.g., boat type) moving in a hypothetical physical environment. Herein, we refer to a numerical characterization of the apparatus and environment as a "load profile." Thus, targeted $T_{load}$ is in general a function both of a load profile and the state of operation of the exercise machine 600, including actual $T_{athlete}$, ω, and all settable and/or intrinsic loads that contribute to the load experienced by the rower 602. The numerical values used to set settable loads in the exercise machine 600 may be influenced by the measured activities of both the rower 602 and other rowers on other machines, real or simulated, hence the ability of various embodiments of the disclosure to produce a joint training experience for rowers on physically separate exercise machines. These general considerations, with other considerations discussed with reference to the illustrative exercise machine 600 shown as a rowing machine, will be understood to apply also, with appropriate modifications, to other forms of exercise machines and athletic apparatus. This disclosure now turns to portions of the closed-loop control method employed by the illustrative exercise machine 600.

As will be clear to persons familiar with electrical machines, the excitation of an alternator, e.g., alternator 618, can be controlled by pulse-width modulation of the excitation current of the field winding, that is, by switching the field-winding voltage on and off at a fixed frequency but with a variable duty cycle. The exercise machine 600 can thus adjust, by altering the duty cycle of a pulse-width-modulated voltage source, the average excitation current of the alternator 618, which in turn affects the torque load placed on the flywheel 616 by the alternator 618 and thus the load experienced by the rower 602. To accomplish this, the controller 632 calculates an estimate of a torque value, $T_{athlete}$, that is applied by the rower 602 to the flywheel 616. The calculation of $T_{athlete}$ is based on several measured variables of machine operation along with a set of pre-recorded variables representing physical characteristics of the exercise machine 600. Calculations can be performed, in various embodiments, using various algorithmic models. In one example, sensors monitor armature voltage $V_{arm}$ of the alternator 618, a field current $I_{fld}$ in the field circuit of the alternator, and a rotational velocity ω of the flywheel 616. The rotational acceleration α of the flywheel 616 can be estimated from repeated measurements of the flywheel rotational velocity ω. Additionally, an armature current $I_{arm}$ of the alternator 618 can be calculated based upon the sensed value of the armature voltage $V_{arm}$. In an example, the power output of the alternator 618 can be between zero (0) and one (1) kilowatt.

The programmed physical characteristics of the exercise machine 600 can include resistance of the electrical load bank, $R_{load}$ (which may in, various embodiments, be a controllable quantity); inductance of the field circuit, $L_{fld}$; resistance of the field $R_{fld}$; resistance of the armature, $R_{arm}$; inductance of the armature, $L_{arm}$; mutual inductance between the armature and the field circuit 38, $L_{af}$ moment of inertia of the flywheel 616, J; and a number of drivetrain damping coefficients, e.g., $b_0$, $b_1$, and $b_2$, so called because they appear in torque terms proportional to powers of ω. The values for $L_{af}$, J, $R_{arm}$, $R_{fld}$, $R_{load}$, $b_0$, $b_1$, and $b_2$ are system characteristics initially identified during design of the exercise machine 600 and can be refined for each individual exercise machine 600 during a calibration process at or near the end of the manufacturing process, or at a later time.

In an example, the controller 632 can use the described values to calculate an estimate of the applied torque value $T_{athlete}$, which can be a sum of a mechanical torque, $T_{mech}$, and an electrical torque, $T_{elec}$, using the following equations:

$$T_{athlete} = T_{mech} + T_{elec} \quad \text{EQUATION 1}$$

where $T_{mech}$ is the sum of an inertial term and several drag terms, i.e., $$T_{mech} = (J \times \alpha) + b_0 + (b_1 \times \omega) + (b_2 \times \omega^2) \quad \text{EQUATION 2}$$

and where $$T_{elec} = L_{af} \times I_{fld} \times I_{arm} \quad \text{EQUATION 3}$$

Note that $T_{elec}$ is proportional to $I_{fld}$, where $I_{fld}$ is a readily controllable quantity, as explained above. Also, $I_{arm}$ may be varied by changing the net resistance of the electrical load bank.

It is to be understood that EQUATIONS 1-3 are illustrative only, and that additional or other variables and equations can be employed to estimate $T_{athlete}$, and that other or additional variables can be sensed to accomplishing the same purpose without departing from the spirit of this disclosure. For example, the current of the armature, $I_{arm}$, can be sensed or measured and used directly in the above $T_{elec}$ equation without sensing or measuring $V_{arm}$ first and then calculating $I_{arm}$ using Ohm's law. Sensing or measuring any number of variables is anticipated by the present disclosure. Persons having skill in the art of electrical engineering will readily understand the above calculations, and also that it is possible to measure a variety of variables to use in various calculations to accomplish the same purpose.

The calculated value for $T_{athlete}$ (e.g., rowing activity; torque actually applied by the athlete) is applied to a dynamic model of a desired load profile (e.g., numerical model of a particular apparatus) to arrive at the appropriate load that the operator should experience. A dynamic model of the exercise machine 600 itself is then referenced for converting the desired load to an appropriate actuation command. For the purposes of this disclosure, an appropriate actuation command can be any number of actions taken by the controller 632 to selectively modify the load experienced by the operator of the exercise machine 600.

In one example, the controller 632 can change at least one value used in one or both of the expressions for $T_{mech}$ and $T_{elec}$ shown above. Changing at least one of the values in these equations changes the load experienced by the operator. For example, the controller 632 can alter the value of one or more of the values J, $b_0$, $b_1$, or $b_2$ of the $T_{mech}$ equation so that the exercise machine 600 feels like an actual watercraft; or, as noted above, $I_{fld}$ and/or $I_{arm}$ may be altered. By comparison, rowing devices according to the prior art can change the torque load on the rower only if a damper is physically (usually manually) moved to increase or decrease an exposed area used for air passage so that a flywheel loaded by a fan shifts its operating point on a continuum between acting as a predominantly inertial load (damper 100% closed) and acting predominantly as a pump (damper 100% open). The closed-loop methods of load control employed in various embodiments of the disclosure allow alteration of operator load at electronic speeds and thus, advantageously, the simulation of rapidly shifting, slowly shifting, and constant real-world loads.

Moreover, the apparatus and methods of various embodiments enable the controller 632 to alter the torque load experienced by the operator to match a selected simulated-apparatus profile. In an example, the calculated $T_{mech}$ has to make up any difference between $T_{elec}$ and the desired torque load $T_{athlete}$ based on the selected profile and state of trainer operation. As shown in EQUATION 2, the value of $T_{mech}$ is a function of velocity and acceleration of the flywheel 616. One method of providing a different load for the exercise machine operator (e.g., rower 602) is to change at least one of the damping coefficients for a given velocity of the flywheel 616 and then change at least one of $I_{fld}$ and $I_{arm}$ to alter $T_{elec}$ so that the actual value of $T_{athlete}$ is equal to or is substantially equal to the desired value of $T_{load}$.

Moreover, the controller 632 can be programmed to replicate the load felt by an operator on any number of actual watercraft or exercise machines. In one example, the described exercise machine 600 can mimic the feel of known rowing machines. In other examples, the described exercise machine 600 can mimic the feel of any number of actual watercraft such as the previously mentioned one-person scull, two-person scull, four-person scull, two-person sweep, four-person sweep, or eight-person sweep. The exercise machine 600 can mimic any number of other watercraft, exercise devices, etc. with each mimicked device represented by a different profile that can be stored in the memory of the controller. Each profile can include changes to any number of the J, $b_0$, $b_1$, and $b_2$ values.

In one example, the process for mimicking a particular device can be described as follows. The dynamic model is in the algorithm as represented in the $T_{mech}$ equation shown above. This model can be similar to some existing rowing machines that provide relatively close approximations of rowing while off the water. The controller 632 then conducts calculations to match the load felt by the operator to what the operator would feel as if they were rowing on the water in a particular watercraft. The controller 632 then applies the resultant load (e.g., $T_{athlete}$) to the dynamic model of the $T_{mech}$ equation. The controller 632 can include memory allocations for the inertia J and damping coefficients $b_0$, $b_1$, and $b_2$ for the separately excited electric machine 618.

For example, the flywheel 616 can be specified, designed, and/or constructed to have particular inertia value J. In some examples, the $b_0$, $b_1$, and $b_2$ damping coefficients are almost negligible. Additionally, in some examples, there can be additional damping coefficients; however, these terms are often not significant enough to substantially affect the calculation result. The controller 632 will then calculate a value for $T_{athlete}$ (the load felt by the operator) using the constants for $L_{af}$, J, $b_0$, $b_1$, and $b_2$.

The controller 632 then accesses a desired torque value for the particular desired profile (e.g., a four-person scull) selected by the operator. Because $T_{elec}$ is controlled, the controller 632 will conduct calculations to augment the $T_{elec}$ value with a new $T_{mech}$ value such that the $T_{athlete}$ is equal to or is substantially close to the desired torque value for the desired profile. In one example, the same $T_{mech}$ and $T_{elec}$ equations are used by the controller 632, except that new values for the inertia and damping coefficients replace the previous ones, for example the equation can use J', $b_0$', $b_1$', $b_2$' rather than J, $b_0$, $b_1$, and $b_2$ to calculate a value for $T_{mech}$. The controller 632 will then add the $T_{elec}$ and the new $T_{mech}$ torque values to ascertain whether actual $T_{athlete}$ is equal to or is substantially close to the desired $T_{athlete}$. If not, the controller 632 can re-calculate $T_{mech}$ using yet another set of inertia and damping coefficients. This process can continue within the controller until an appropriate $T_{athlete}$ value is attained.

The controller 632 then applies the known inertia and damping coefficients to the $T_{mech}$ equation to make the exercise machine 600 "feel like" the selected apparatus (e.g., a four-person scull). Each actual apparatus moves very differently on the water; e.g., it is to be appreciated that a one-person apparatus can exhibit relatively fast acceleration values and have a relatively low top speed on the water. Another apparatus, such as an eight-person apparatus, can exhibit relatively slow acceleration and have a relatively high top speed. The $T_{mech}$ equation shown above can mimic each of the apparatus and their various characteristics with the proper values for J, $b_0$, $b_1$, and $b_2$.

It is to be appreciated from the above equations that the torque load the operator experiences ($T_{athlete}$) is a function of the current at the armature ($I_{arm}$), which can be calculated after measuring or sensing $V_{arm}$, and of the current through the field circuit ($I_{fld}$), which is a closed loop control variable. The controller 632 constantly measures and adjusts the $I_{fld}$ modulator to produce the desired $T_{athlete}$. In one example, if $I_{fld}$ is higher than the value required to replicate the selected profile, the controller 632 can decrease the duty cycle of $I_{fld}$ to reduce the average (effective) $I_{fld}$. Similarly, the controller 632 can increase the duty cycle if the value of $I_{fld}$ is too low. The controller 632 can monitor and adjust $I_{fld}$ at relatively short intervals such that $I_{fld}$ is adjusted as needed. In this way, $I_{fld}$ is controlled such that the exercise machine 600 can approximate real-world conditions of various rowing apparatus as described above.

Referring again to FIG. 6B, in one example, wherein the exercise machine is in at least some modes of operation self-powering, the battery 638 can provide the controller 632 with electrical power. Additionally, the battery 638 can provide power to the field circuit of the alternator 618 for a relatively short time as the rower 602 begins to operate the exercise machine. Once the operator 602 begins moving the connective structure 610 (e.g., by rowing), the electrical converter 636 will replenish electrical charge removed from the battery 638 while the operator 602 completes one or more strokes during an exercise period. In an example, electrical energy can be diverted from the electrical circuit of the electric machine 618 before the electrical signal reaches the electrical load bank 626, and the diverted electrical energy can be supplied to the battery 638. In another example, the battery 638 can draw power from the electrical load bank 626 to maintain a charge. As an alternative, a standard wall power supply (e.g., 110-volt supply, not depicted) can be used to provide power to the battery 638. In yet another example, a battery charger can accept electrical supply from a combination of the standard wall power supply and the electrical energy created by operating the exercise machine 600.

The exercise machine 600 can communicate with at least one additional associated exercise machine (e.g., via the direct-interconnect topology of FIG. 4A, the centralized topology of FIG. 5, or some other topology). Communication between exercise machines can provide the benefit of having multiple operators working out on multiple machines against an effectively shared load. For example, an operator in one location can operate an exercise machine set to a desired load profile to replicate a four-person scull, while three additional operators can operate three additional exercise machines with the same desired load profile, each operator working against the same load. In an example, the exercise machine 600 exchanges activity data with each of the three associated exercise machines, and this data can be incorporated in controller and/or server calculations to achieve desired closed-loop control characteristics.

Various suitable algorithms can incorporate various data items, including activity data from multiple machines, to achieve desired closed-loop control characteristics with the apparatus and methods of the present disclosure. In an example where machine 600 is one of P comparable exercise machines (e.g., with similar flywheels) combined virtually in a group-training fashion, using the inertia J of the flywheel 616 and the desired acceleration $\alpha_{des}$ of the flywheel 616, one can calculate a net torque, $T_{net}$, acting on the flywheel 616 using $$T_{net} = J \times \alpha_{des}$$

Solving for desired rotational acceleration $\alpha_{des}$, one obtains:

$$\alpha_{des} = T_{net}/J$$

If the desired rotational velocity of the flywheels of the P machines is $\omega_{des}$, then, integrating with respect to time, $$\omega_{des} = \int \alpha_{des}$$

This can be combined with all known applied torque(s) from each of the associated exercise machines to determine a desired rotational velocity, $\omega_{des}$, for the flywheels using desired damping coefficients $b_{0des}$, $b_{1des}$, and $b_{2des}$:

$$\omega_{des} = \int((T_{crew} - \{b_{0des} + (b_{1des} \times \omega) + (b_{2des} \times \omega^2)\})/J_{des}) \quad \text{EQUATION 4}$$

In EQUATION 4, $J_{des}$ is the desired flywheel inertia, $\omega$ is the actual rotational velocity of the flywheel, and $$T_{crew} = \Sigma T_{athlete}(i)/P, \ i=1, \ldots P$$

where $T_{athlete}(i)$ is the torque applied by the ith of the P athletes.

$T_{net}$ in the above description is the desired $T_{load}$, and, the $T_{crew}$ term can be calculated for an arbitrary number of athletes as appropriate.

EQUATION 4 can be used to directly perform closed loop speed control. Any number of closed loop control methodologies can be applied to achieve desired closed loop control characteristics. Examples of closed-loop control methodologies can include, but are not limited to: proportional-integral-derivative control, lag-compensation, h-infinity, state-space, etc.

Many activities are enabled by the foregoing and various other embodiments of the disclosure that were not enabled at all, or were enabled less conveniently or more expensively, by the prior art. A non-exhaustive list of illustrative use cases is hereby presented to illustrate the highly flexible potential of embodiments of the disclosure:

- An athlete may exercise on an isolated exercise machine at a fixed load level without engaging a load profile (virtual apparatus): that is, the athlete may engage in normal stand-alone machine exercise, as on a typical prior-art machine.
- An athlete may exercise on an isolated exercise machine which simulates the load profile of a specific athletic apparatus.
- An athlete may exercise on a networked exercise machine as part of a virtual team of other real athletes on other exercise machines jointly operating a specific virtual apparatus, where the athletes involved may be at various geographical distances from each other.
- An athlete may exercise as part of a virtual team of whose other members one or more are simulated.
- Athletes may be combined and recombined by manipulation of appropriate software into various teams of various sizes operating various virtual apparatuses, and/or moved between virtual positions in a given virtual apparatus.

A virtual team of real athletes may compete against one or more virtual teams, whose members may be partly or entirely real or partly or entirely simulated.

Having described the foregoing embodiments of the disclosure, it will be apparent to those of ordinary skill in the art that other embodiments incorporating the concepts disclosed herein may be used without departing from the spirit and scope of the disclosure. The described embodiments are to be considered in all respects as only illustrative and not restrictive.

The invention claimed is:

1. A rowing exercise machine, comprising:
   a mechanical energy storage device;
   a handle coupled to the mechanical energy storage device via a connective structure wherein relative movement of the handle with respect to the mechanical energy storage device urges motion of the mechanical energy storage device;
   an apparatus configured to dynamically supplement a resistance of the mechanical energy storage device with an added resistance; and
   a controller in communication with the mechanical energy storage device and the apparatus, the controller having computer readable instructions to determine the added resistance and to dynamically and selectively adjust the added resistance to alter a load experienced by a rower participating in a group exercise by applying force to the handle; and
   a communication pathway between the controller of the rowing exercise machine and a controller of at least one additional associated rowing exercise machine that permits application of the forces applied in each of the rowing machines to a shared load of a multi-rower watercraft.

2. The rowing exercise machine of claim 1, wherein the shared load of a multi-rower watercraft is one of a two person scull or a four person scull.

3. The rowing exercise machine of claim 1, wherein the shared load of a multi-rower watercraft is one of a two person sweep, a four person sweep, or an eight person sweep.

4. The rowing exercise machine of claim 1, wherein the apparatus comprises an electrical load bank.

5. The rowing exercise machine of claim 1, wherein the communication pathway comprises a network topology.

6. The rowing exercise machine of claim 1, further comprising an apparatus configured to provide visual indication of an action taking place on the at least one additional associated exercise machine.

7. The rowing exercise machine of claim 1, further comprising a user interactive apparatus configured to provide aural indication of an action taking place on the at least one additional associated exercise machine.

8. The rowing exercise machine of claim 1, wherein the rower is participating in a group exercise performed in a simulated multi-rower watercraft against a workload shared with at least one other rower.

9. The rowing exercise machine of claim 8, wherein the at least one other rower is a real rower operating another rowing machine as part of the group exercise.

10. The rowing exercise machine of claim 1, wherein the handle is configured to replicate a handle of an oar used when the multi-rower watercraft is one of a two person scull or a four person scull.

11. The rowing exercise machine of claim 1, wherein the handle is configured to replicate a handle of an oar used when the multi-rower watercraft is one of a two person sweep, a four person sweep, or an eight person sweep.

12. The rowing exercise machine of claim 1, further comprising an electrical generator.

13. The rowing exercise machine of claim 12, wherein the electrical generator is an electric machine and wherein the controller further comprises computer readable instructions for adapting a responsiveness of the electric machine based on a watercraft apparatus selected for the group exercise.

14. The rowing exercise machine of claim 1, wherein the mechanical energy storage device is a flywheel.

15. The rowing exercise machine of claim 1, wherein the controller selectively modifies the load experienced by the rower to simulate rapidly shifting, slowly shifting, and constant real world loads of the multi-rower watercraft as influenced by an individual effort of each of the rowers in the multi-rower watercraft.

16. The rowing exercise machine of claim 15, wherein the controller adjusts and then applies one or more drive train damping coefficients to the load experienced by the rower in response to the sum of the individual efforts of the rowers in the multi-rower watercraft, in the multi-rower watercraft.

17. A kit for modifying an existing rowing machine, comprising:
   an electric machine;
   a mechanical energy storage device;
   a transmission for coupling the electric machine to the mechanical energy storage device;
   an electrical load bank to be coupled to the electric machine;
   a controller to be placed in communication with the electric machine and the electric load bank and having computer readable instructions to selectively adapt an operation of the electric machine or the electric load bank to provide a dynamic selective alteration of a load experienced by a user of the rowing machine; and
   an electronic memory in communication with the controller, the electronic memory containing computer readable instructions having load characteristics of a multi-rower watercraft, providing a shared load to one or more associated rowing machines,
   wherein the kit components are used to modify an associated existing exercise machine thereby enabling field upgrade of said associated existing exercise machine to be capable of communication with at least one additional associated exercise machine, wherein a total resistance in said associated exercise machine is duplicated in an additional associated exercise machine such that a first rower operating said exercise machine and a second rower operating said additional associated exercise machine operate as a virtual team.

* * * * *